US006735784B2

(12) United States Patent
Isom et al.

(10) Patent No.: US 6,735,784 B2
(45) Date of Patent: May 18, 2004

(54) APPARATUS AND METHOD FOR MAKING AN EAR WARMER AND AN EAR WARMER FRAME

(75) Inventors: Matthew Isom, Baltimore, MD (US); Brian E. Le Gette, Baltimore, MD (US); Alan Tipp, Baltimore, MD (US); Justin Saul Werner, Millersville, MD (US); Ronald L. Wilson, II, Catonsville, MD (US)

(73) Assignee: 180s, Inc., Baltimore, MD (US)

( * ) Notice: Subject to any disclaimer, the term of this patent is extended or adjusted under 35 U.S.C. 154(b) by 0 days.

(21) Appl. No.: 10/056,093

(22) Filed: Jan. 28, 2002

(65) Prior Publication Data

US 2003/0140397 A1 Jul. 31, 2003

(51) Int. Cl.$^7$ ................................................. A42B 1/06
(52) U.S. Cl. .......................................................... 2/209
(58) Field of Search ..................... 2/209, 183, DIG. 11; 381/379, 383, 378, 373, 371, 381; 128/864, 866, 867; 181/129, 133, 137

(56) References Cited

U.S. PATENT DOCUMENTS

| | | | |
|---|---|---|---|
| 138,894 A | | 5/1873 | Isidor |
| 548,738 A | | 10/1895 | Ballard |
| 804,731 A | * | 11/1905 | Keller ........................... 2/209 |
| 953,623 A | | 3/1910 | Keller |
| 1,179,473 A | | 4/1916 | Taylor |
| 1,326,875 A | | 12/1919 | Miller |
| 1,398,958 A | | 12/1921 | Basch |
| 1,577,183 A | | 3/1926 | Dowiarz |
| 1,628,483 A | | 5/1927 | Wiegand et al. |
| 1,988,880 A | | 1/1935 | Strouse |
| 2,070,216 A | | 2/1937 | Rosenberg |
| 2,216,954 A | | 10/1940 | McDonough |
| 2,246,031 A | | 6/1941 | Baritz et al. |

(List continued on next page.)

FOREIGN PATENT DOCUMENTS

| | | | |
|---|---|---|---|
| CH | 294003 | 1/1954 | |
| EP | 745364 A2 | * 12/1996 | ........... A61F/11/14 |
| FR | 1 353 524 | 1/1964 | |
| FR | 2 532 838 A1 | 3/1984 | |
| FR | 2 536 253 A | 5/1984 | |
| GB | 1 327 614 | 8/1973 | |
| JP | 60-29141 | 2/1985 | |
| JP | 60-244188 A | 12/1985 | |
| JP | 62-21016 | 2/1987 | |
| JP | 63-20232 | 6/1988 | |
| JP | 63-21972 | 8/1989 | |
| JP | 6-41720 | 6/1994 | |
| JP | 6-351090 A | 12/1994 | |
| JP | 10257581 | 8/2000 | |
| JP | 2002-11036 A | 1/2002 | |
| WO | WO 01/76402 A1 | 10/2001 | |

OTHER PUBLICATIONS

Le Gette, et al., U.S. Patent Application Publication No. US 2002/0026661 A1, Mar. 7, 2002, "Apparatus and Method for Making an Ear Warmer and an Ear Warmer Frame," (U.S. patent application Ser. No. 09/986,103; filed Nov. 7, 2001).

Le Gette, et al., U.S. Patent Application Publication No. US 2002/0020003 A1, Feb. 21, 2002, "Apparatus and Method for Making an Ear Warmer Having Interior Seams," (U.S. patent application Ser. No. 09/978,591; filed Oct. 18, 2001).

Le Gette, et al., "Ear Protection Device," Specification and drawings of U.S. patent application Ser. No. 10/024,523, filed Dec. 21, 2001.

Advertisement: The "PODZ" ear warming eye glass retainer, Shred Alert Products of Hood River, Oregon.

Primary Examiner—Rodney M. Lindsey
(74) Attorney, Agent, or Firm—Cooley Godward LLP

(57) ABSTRACT

The present invention relates to an ear warmer device. More specifically, the present invention relates to apparatus and methods for making ear warmers and ear warmer frames.

21 Claims, 15 Drawing Sheets

U.S. PATENT DOCUMENTS

| | | | |
|---|---|---|---|
| 2,314,782 A | 3/1943 | Goretsky | |
| 2,333,392 A | 11/1943 | Rosenweig | |
| 2,405,326 A | 8/1946 | Plotsky | |
| 2,420,245 A | 5/1947 | Hurst | |
| 2,532,852 A | 12/1950 | Oaks | |
| 2,586,644 A | 2/1952 | Gilbert | |
| 2,615,169 A | 10/1952 | Maxant | |
| 2,671,221 A | 3/1954 | Triplett | |
| 2,717,930 A | 9/1955 | Hintz | |
| 2,776,436 A * | 1/1957 | Berg | 2/209 |
| 2,858,544 A | 11/1958 | Roth | |
| 3,087,028 A | 4/1963 | Bonnin | |
| 3,119,119 A * | 1/1964 | Millinger et al. | 2/209 |
| 3,156,923 A | 11/1964 | Timm | |
| 3,249,949 A | 5/1966 | Rosenberg et al. | |
| 3,308,480 A | 3/1967 | Elder | |
| 3,447,160 A | 6/1969 | Teder | |
| 3,509,580 A | 5/1970 | Rubenstein et al. | |
| 3,787,899 A | 1/1974 | Krawagna | |
| 4,065,176 A | 12/1977 | Fontana | |
| 4,277,847 A | 7/1981 | Florio | |
| 4,404,434 A | 9/1983 | Pelt et al. | |
| 4,445,005 A | 4/1984 | Furuhashi | |
| 4,463,223 A | 7/1984 | Yamanoi et al. | |
| 4,516,274 A | 5/1985 | Buckland | |
| 4,542,803 A | 9/1985 | Houng | |
| 4,546,215 A | 10/1985 | Ferraro | |
| 4,615,185 A | 10/1986 | Bollinger | |
| 4,654,898 A | 4/1987 | Ishikawa | |
| 4,660,229 A | 4/1987 | Harris | |
| 4,662,590 A | 5/1987 | Hungerford, Jr. | |
| 4,669,129 A | 6/1987 | Chance | |
| 4,670,911 A | 6/1987 | Dunford | |
| 4,727,599 A | 2/1988 | Rappaport et al. | |
| 4,747,145 A | 5/1988 | Wiegel | |
| 4,776,042 A | 10/1988 | Hanson et al. | |
| 4,776,044 A | 10/1988 | Makins | |
| 4,783,822 A | 11/1988 | Toole et al. | |
| 4,791,684 A | 12/1988 | Schwartz | |
| 4,858,248 A | 8/1989 | Goldsmith et al. | |
| 4,864,619 A | 9/1989 | Spates | |
| 4,872,219 A | 10/1989 | Duncan | |
| 4,907,266 A | 3/1990 | Chen | |
| 4,918,757 A | 4/1990 | Janssen et al. | |
| 4,982,451 A | 1/1991 | Graham | |
| 5,033,094 A | 7/1991 | Hung | |
| 5,038,412 A | 8/1991 | Cionni | |
| 5,117,464 A | 5/1992 | Jones et al. | |
| 5,164,987 A | 11/1992 | Raven | |
| 5,201,856 A | 4/1993 | Edwards | |
| 5,257,420 A | 11/1993 | Byrne, Jr. | |
| 5,327,178 A | 7/1994 | McManigal | |
| 5,339,467 A | 8/1994 | Brinkley | |
| 5,545,859 A | 8/1996 | Ullrich | |
| 5,551,089 A | 9/1996 | Whidden | |
| 5,749,099 A | 5/1998 | Voorhees | |
| 5,821,468 A | 10/1998 | Urella et al. | |
| 5,835,609 A | 11/1998 | LeGette et al. | |
| 6,016,574 A | 1/2000 | Chen | |
| 6,065,157 A | 5/2000 | Felman | |
| 6,104,824 A | 8/2000 | Ito | |
| 6,332,223 B1 | 12/2001 | Le Gette et al. | |
| 2003/0091209 A1 * | 5/2003 | Ito et al. | 381/379 |

* cited by examiner

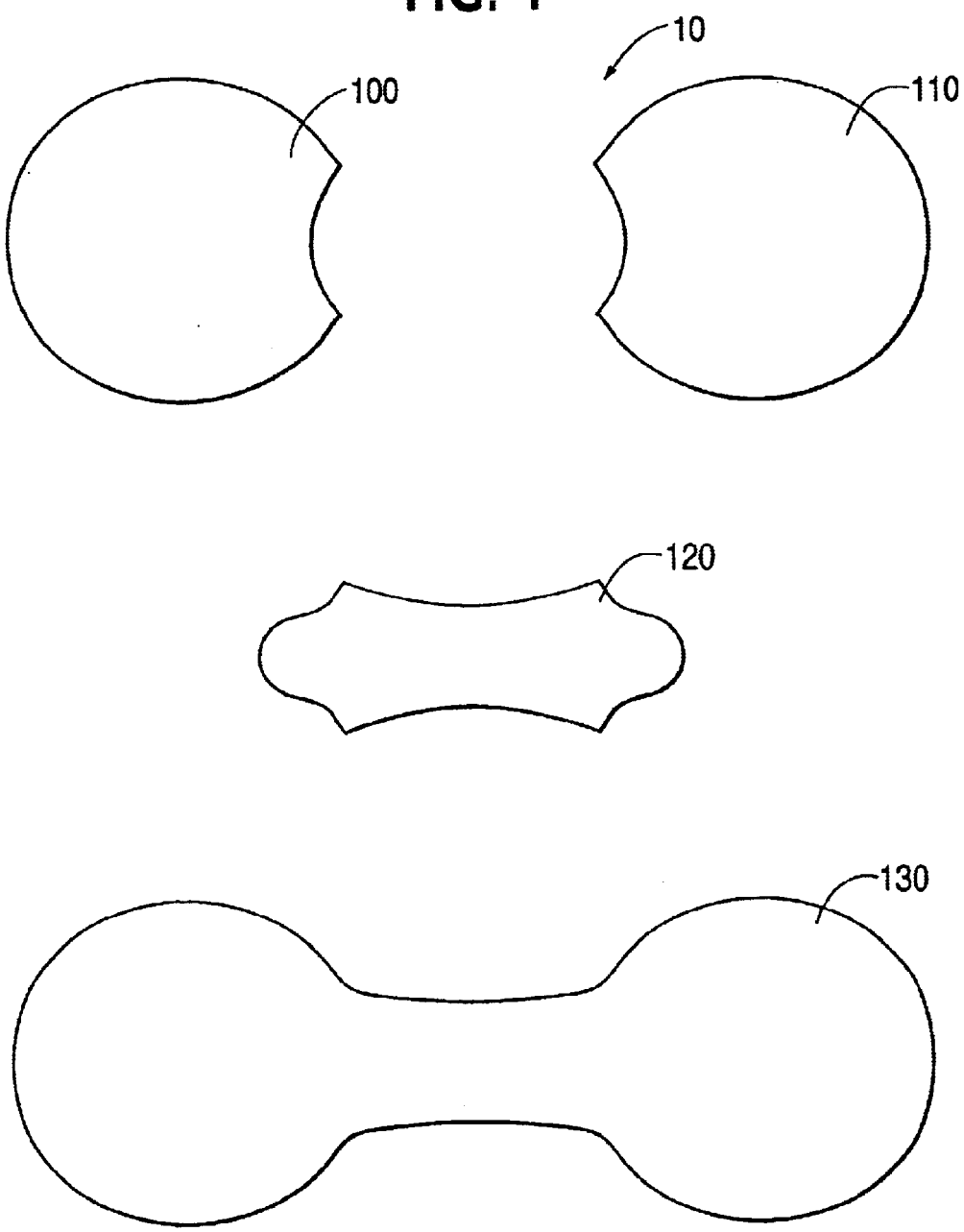

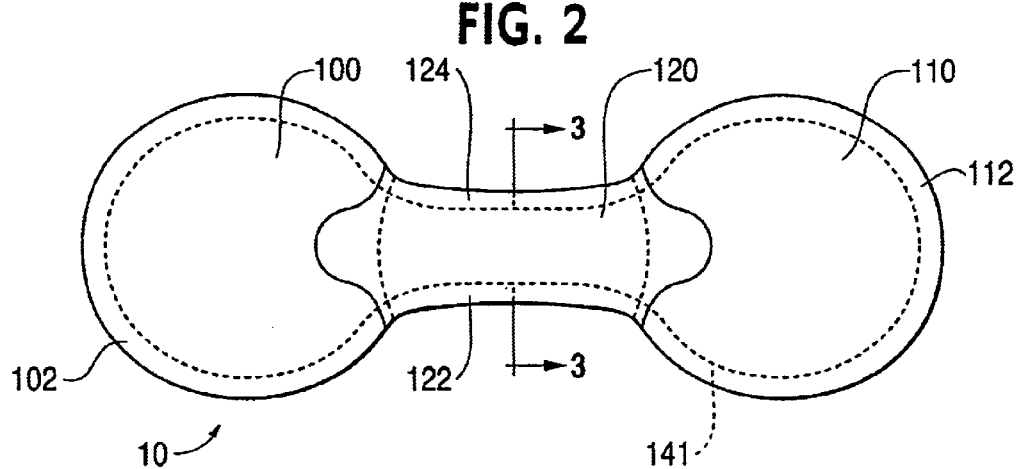
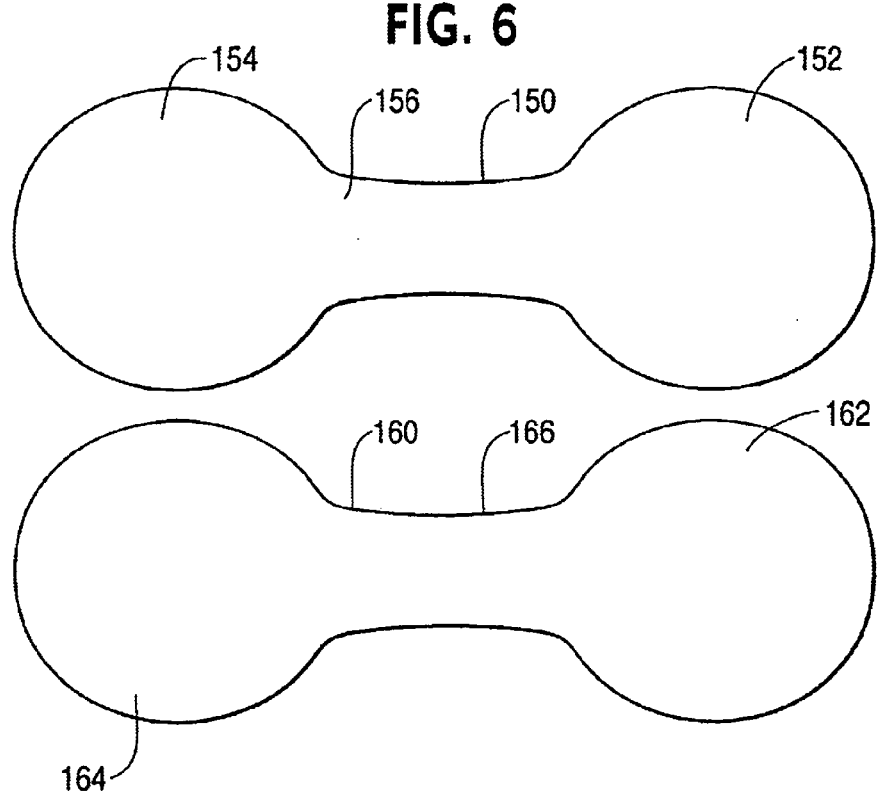

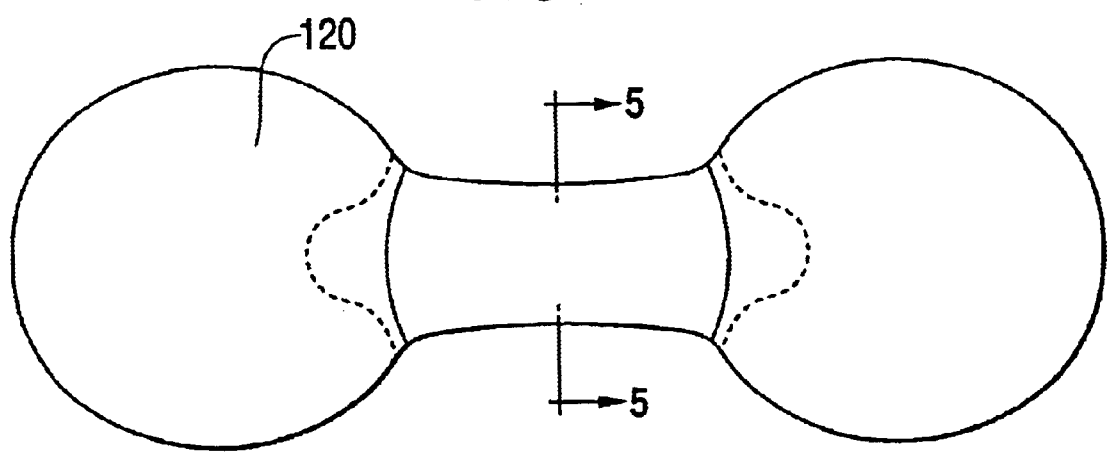

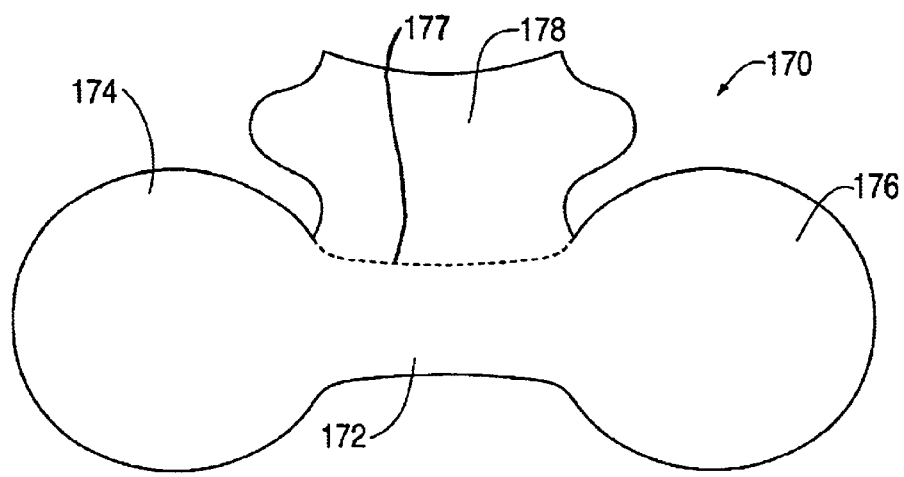
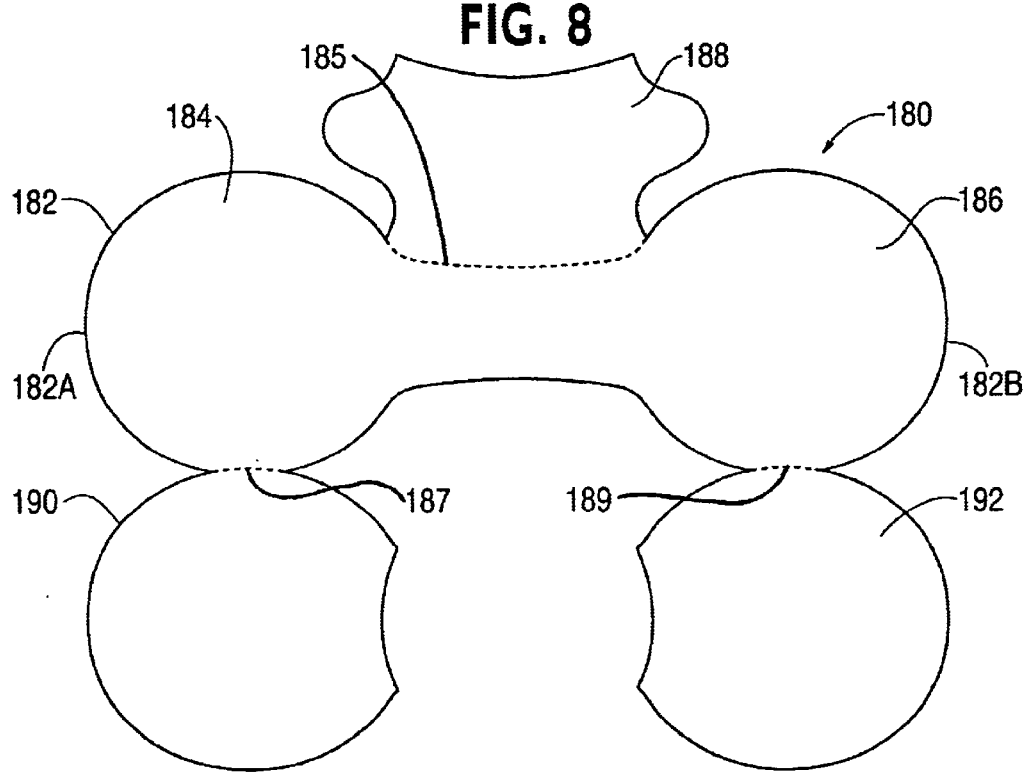

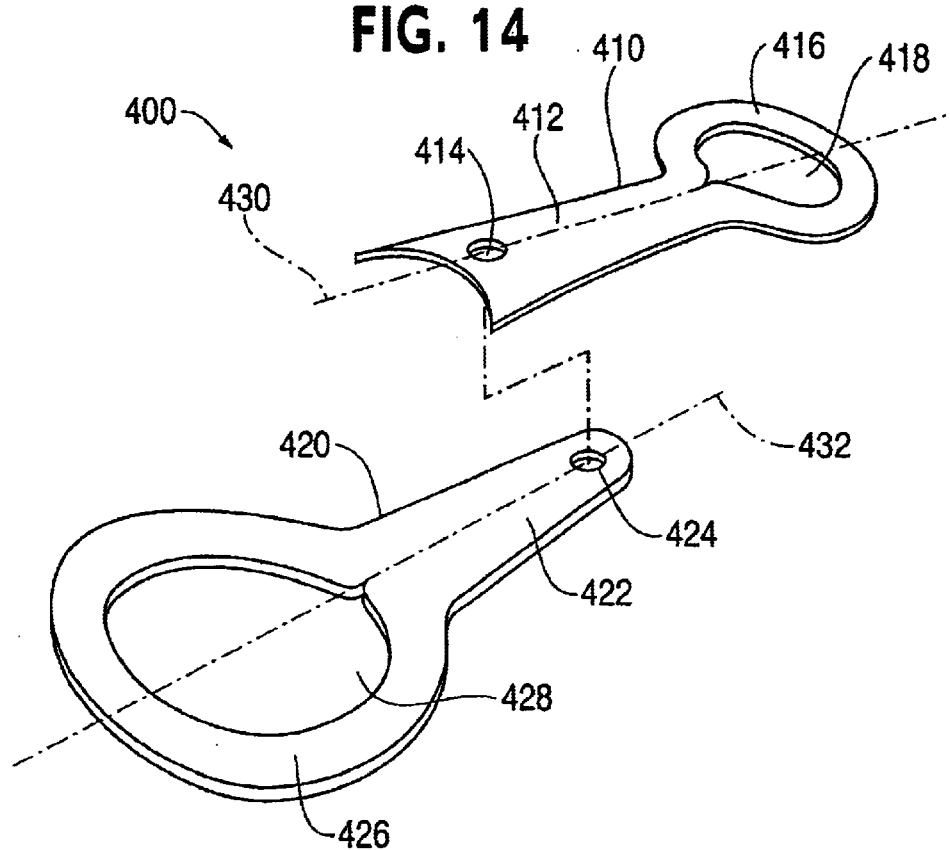
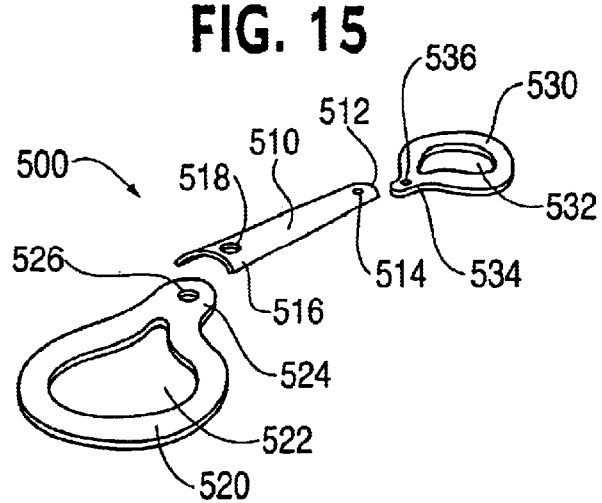

APPARATUS AND METHOD FOR MAKING AN EAR WARMER AND AN EAR WARMER FRAME

CROSS REFERENCE TO RELATED APPLICATIONS

This application is related to U.S. patent application Ser. No. 09/986,103, entitled "Apparatus and Method for Making an Ear Warmer and an Ear Warmer Frame," filed Nov. 7, 2001; U.S. patent application Ser. No. 09/978,591, entitled "Apparatus and Method for Making an Ear Warmer Having Interior Seams," filed Oct. 18, 2001; International Application Serial No. PCT/US01/11041, entitled "Apparatus and Method For Making an Ear Warmer and an Ear Warmer Frame," filed Apr. 5, 2001, and published as International Publication No. WO01/76402A1 on Oct. 18, 2001; and U.S. patent application Ser. No. 09/521,241, entitled "Apparatus and Method for Making an Ear Warmer Having Interior Seams," filed Apr. 5, 2000, now U.S. Pat. No. 6,332,223 B1. The disclosures of each of these applications are incorporated by reference in their entirety.

BACKGROUND OF THE INVENTION

The present invention relates to an ear warmer device. More specifically, the present invention relates to apparatus and methods for making ear warmers and ear warmer frames.

SUMMARY OF THE INVENTION

In one embodiment, an ear warmer comprises a set of membranes and a frame. The membranes are coupled together to form a shell into which the frame is inserted. In an alternative embodiment, an ear warmer comprises a single membrane and a frame. The single membrane is folded or configured to define a shell into which the frame is inserted. In one embodiment, the frame is a single frame member. In alternative embodiments, the frame includes multiple components.

BRIEF DESCRIPTION OF THE DRAWINGS

FIG. 1 illustrates a set of membranes for use in constructing an ear warmer, according to an embodiment of the present invention.

FIG. 2 illustrates an arrangement of the ear warmer shell of FIG. 1 during an interim step in an assembly process.

FIG. 4 illustrates an arrangement of an ear warmer shell according to an embodiment of the present invention.

FIG. 6 illustrates a set of membranes for use in constructing an ear warmer, according to another embodiment of the present invention.

FIG. 7 illustrates a membrane for use in constructing an ear warmer, according to another embodiment of the present invention.

FIG. 8 illustrates a membrane for use in constructing an ear warmer, according to another embodiment of the present invention.

FIG. 14 illustrates an exploded perspective view of a frame for use in constructing an ear warmer, according to another embodiment of the invention.

FIG. 15 illustrates an exploded perspective view of a frame for use in constructing an ear warmer, according to another embodiment of the invention.

DETAILED DESCRIPTION OF THE INVENTION

Figure 3:
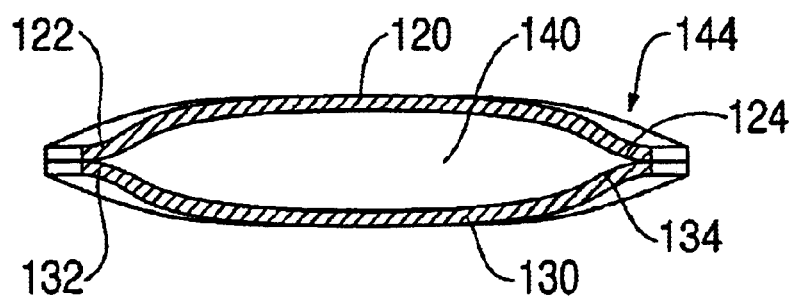
FIG. 3 illustrates a cross-sectional view of the ear warmer shell of FIG. 2 taken along the lines "3—3" in FIG. 2.

In one embodiment, an ear warmer comprises a set of membranes and a frame. The membranes are coupled together to form a shell into which the frame is inserted. In an alternative embodiment, an ear warmer comprises a single membrane and a frame. The single membrane is folded or configured to define a shell into which the frame is inserted. In one embodiment, the frame is a single frame member. In alternative embodiments, the frame includes multiple components.

FIG. 1 illustrates a set of membranes for use in constructing an ear warmer, according to an embodiment of the present invention. As shown in FIG. 1, an ear warmer shell 10 can be constructed from a first ear membrane 100, a second ear membrane 110, a middle membrane 120, and an outer membrane 130. Membranes 100 through 130 can be made of various types of material appropriate for providing warmth while also being comfortable on the wearer's skin. For example, membranes 100 through 130 can be made of such materials as fleece, wool, cotton, foam and/or neoprene.

FIG. 2 illustrates an arrangement of the ear warmer shell of FIG. 1 during an interim step in one assembly process. Ear warmer shell 10 includes an arrangement of membranes 100 through 130. In this arrangement, membranes 100 through 130 are disposed proximate to each other.

In the illustrated embodiment, ear warmer shell 10 can be constructed by first disposing first ear membrane 100 and second ear membrane 110 on top of outer membrane 130. Middle membrane 120 can then be placed on top of the set of outer membrane 130, ear membrane 100 and ear membrane 110 in the arrangement shown in FIG. 2. Ear membranes 100 and 110, and middle membrane 120 are on top of each other and outer membrane 130 in the sense that they are ordered in a particular way; the particular orientation of the collection of membranes as shown in the figures herein are not important. The arrangement of membranes 100 through 130 can then be coupled or attached along the perimeter of ear warmer shell 10 via attachment 141.

This arrangement of membranes 100 through 130 can thus be coupled or attached along the perimeter of ear warmer shell 10 and covered with a binding (not shown). In an alternative embodiment for assembling the membranes illustrated in FIG. 2, the middle membrane 120 can be placed on the outer membrane 130 and the ear membranes 100 and 110 can be placed on the middle membrane 120 and the outer membrane 130.

A variety of couplings or processes can be used to secure the membranes together. For example, returning to the illustrated embodiment of FIG. 2, portions of the ear membranes 100 and 110 and middle membrane 120 can be bound to outer membrane 130. The membranes 100, 110, 120, and 130 can be coupled together. Any combination of sewn, bound, or any other couplings can be used. Exemplary methods of assembling the membranes are disclosed in U.S. patent application Ser. No. 09/521,241, the disclosure of which is incorporated by reference in its entirety.

FIG. 3 illustrates a cross-sectional view of the ear warmer shell of FIG. 2. In the illustrated embodiment, each membrane includes a side along a portion of the perimeter of that particular membrane. For example, ear membrane 100 includes side 102, ear membrane 110 includes side 112, middle membrane 120 includes sides 122 and 124, and outer membrane 130 includes sides 132 and 134. The middle membrane 120 and the outer membrane 130 are disposed proximate to each other so that the middle membrane sides 122 and 124 are proximate to corresponding sides 132 and 134 of the outer membrane 130. Side 122 of the middle membrane 120 is aligned with side 132 of the outer membrane 130. Similarly, side 124 of the middle membrane 120 is aligned with side 134 of the outer membrane 130. The corresponding sides of the other membranes or membrane portions are placed proximate to each other as well.

In the illustrated embodiment, the sides of the membranes are coupled together and the membranes are turned inside out as disclosed in U.S. patent application Ser. No. 09/521,241.

A top view of an embodiment of an inverted ear warmer shell is illustrated in FIG. 4. As illustrated, the sides of the membranes and any coupling of the membranes are not apparent from the exterior of the ear warmer shell and are located in the interior of the ear warmer shell.

Figure 5:
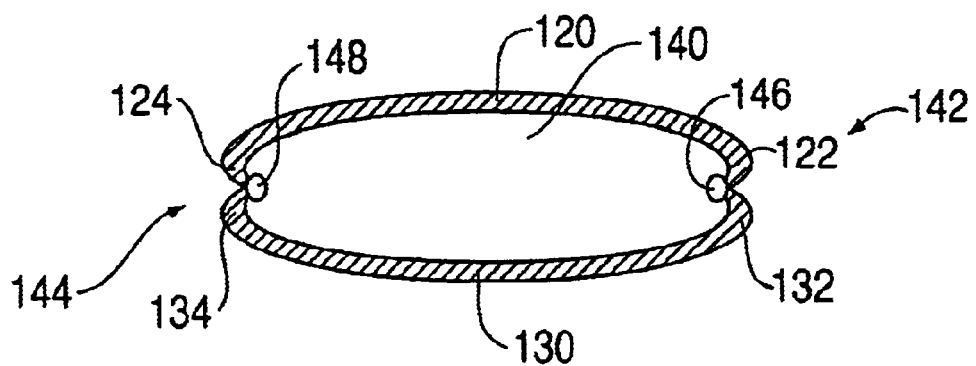
FIG. 5 illustrates a cross-sectional view of the ear warmer shell of FIG. 4 taken along the lines "5—5" in FIG. 4.

FIG. 5 illustrates a cross-sectional view of the ear warmer shell of FIG. 4. In the illustrated embodiment, the corresponding sides of the membranes adjacent to each other are fixedly coupled together prior to the membranes being inverted to the positions illustrated in FIGS. 4 and 5. For example, sides 122 and 132 are coupled or bound together to form a fixedly coupled portion 146. Similarly, sides 124 and 134 are coupled together to form a fixedly coupled portion 148. The term "fixedly coupled portion" includes any type of connection or attachment that if pulled apart would result in damage to the membranes. The ear membranes 100 and 110 are similarly coupled to the middle membrane 120 and the outer membrane 130.

In alternative embodiments, the corresponding sides of the membranes adjacent to each other are removably coupled together. For example, the sides can be coupled together using mating connectors, such as hook and loop fasteners, snaps, etc.

In the illustrated embodiment, the membranes 100, 110, 120, and 130 are coupled together to form fixedly coupled portions 146 and 148 using radio frequency welding. As a result, the fixedly coupled portion 146 includes a weld that couples the middle membrane side 122 and the outer membrane side 132. Similarly, the fixedly coupled portion 148 includes a weld that couples the middle membrane side 124 and the outer membrane side 134. In alternative embodiments, the membranes 100, 110, 120, and 130 may be coupled together using any type of welding or any other process that couples the membranes together.

Once the membranes have been coupled together, the membranes are turned inside out, as described above and as illustrated in FIGS. 4 and 5. As illustrated, the fixedly coupled portions 146 and 148 are disposed within the interior 140 of the ear warmer shell.

FIG. 6 illustrates an alternative shell for use in constructing an ear warmer according to another embodiment of the present invention. Inner membrane 150 includes ear portions 152 and 154 and a middle portion 156. Outer membrane 160 includes ear portions 162 and 164 and a middle portion 166. Inner membrane 150 and outer membrane 160 may be coupled using any technology, including, for example, radio frequency welding.

FIG. 7 illustrates a membrane for use in constructing an ear warmer, according to another embodiment of the present invention. Similar to the outer membrane 130 and the middle membrane 120 shown in FIG. 1, FIG. 7 illustrates a membrane 170 having multiple portions, including an outer portion 172 and a middle portion 178. An ear warmer shell can be arranged as follows. First, the ear membranes (e.g., ear membranes 100 and 110, not shown in FIG. 7) can be placed on the corresponding portions 174 and 176, respectively, of outer portion 172. Middle portion 178 can then be folded on to outer portion 172 and the ear membranes along the line 177. The collective perimeter can then be bound, welded, or sewn and the membranes can be turned inside out as described in U.S. patent application Ser. No. 09/521,241.

In an alternative embodiment for assembling the membranes shown in FIG. 7, the membranes are not turned inside out. For example, the middle portion 178 can be folded onto the outer portion 172 and the ear membranes subsequently placed on the outer portion 172 and the middle portion 178. The collective perimeter can then be bound, welded, or sewn.

FIG. 8 illustrates a membrane for use in constructing an ear warmer, according to another embodiment of the present invention. Similar to ear membrane 100, ear membrane 110, middle membrane 120 and outer membrane 130 shown in FIG. 1, FIG. 8 illustrates a membrane 180 having an ear portion 190, an ear portion 192, a middle portion 188, and an outer portion 182.

In the illustrated embodiment of FIG. 8, the membrane portions can be arranged as follows. First, ear portion 190 can be folded on to the corresponding portion 184 of the outer portion 182 along line 187. Similarly, ear portion 192 can be folded on to the corresponding portion 186 of the outer portion 182 along line 189. Middle portion 188 can then be folded on to outer portion 182 and ear portions 190, 192 along the line 185. The collective perimeter can then be bound, welded, or sewn and the membranes can be turned inside out.

In an alternative embodiment for assembling the membranes of FIG. 8, the membranes are not turned inside out. For example, the middle portion 188 can be folded onto the outer portion 182 along the line 185. The ear portions 190 and 192 can be folded on to the outer portion corresponding portions 184 and 186, respectively. The collective perimeter can then be bound, welded, or sewn.

Rather than the separate membranes shown in FIG. 1, variations to FIGS. 7 and 8 are possible where certain membranes are integrally formed together and folded over. For example, in other embodiments, only one ear membrane is integrally formed with the outer membrane, only two ear membranes are integrally formed with the outer membrane, or only one ear membrane and the middle membrane are integrally formed with the outer membrane.

In an alternative embodiment, the membranes can be integrally formed together at various locations (e.g., discontinuous locations) rather than along the entire fold (such as line 177 shown in FIG. 7). In another embodiment, the membranes can be integrally formed at various locations relative to the outer portion of the membrane. For example, rather than the ear portions being integrally formed at the lower location of the outer portion (as shown in FIG. 8), the ear portions can be integrally formed with the outer portion at other locations, such as the side locations 182A and 182B of the outer portion 182. The various locations that are possible are those where the portions of the membrane (i.e., the middle portion, and/or the ear portions) fold on to the outer portion of the membrane to appropriately form the ear warmer shell.

Figure 9:
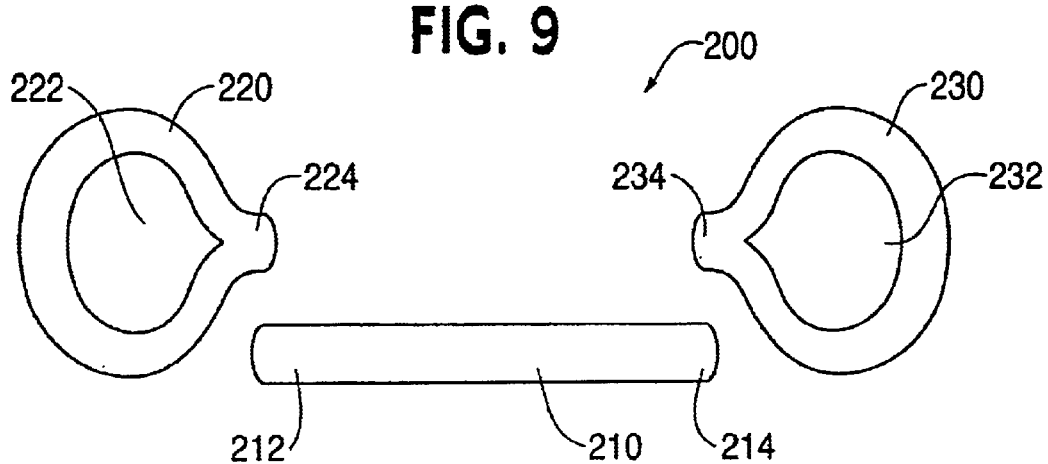
FIG. 9 illustrates an exploded top view of a frame for use in constructing an ear warmer, according to another embodiment of the present invention.
Figure 10:
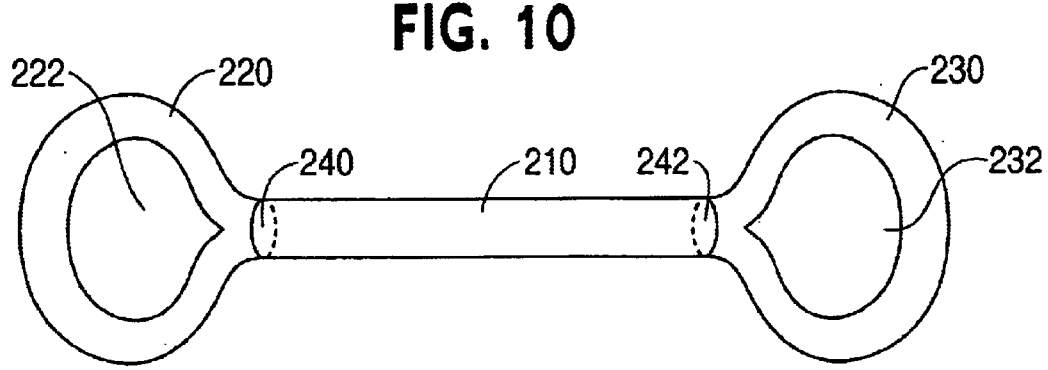
FIG. 10 illustrates an assembled top view of a frame of FIG. 9.

FIGS. 9 and 10 illustrate a frame for use in constructing an ear warmer, according to another embodiment of the present invention. Frame 200 includes a band 210 and ear frame members 220 and 230. Band 210 can be coupled to ear frame members 220 and 230 using any conventional technique to form a frame for an ear warmer.

In the illustrated embodiment, band 210 is an elongate member with ends 212 and 214. As illustrated in FIG. 9, ear frame member 220 defines an opening 222 and includes an end 224. Similarly, ear frame member 230 defines an opening 232 and includes an end 234.

As illustrated in FIG. 10, end 224 of ear frame member 220 is coupled to end 212 of the band 210 at connection 240. Similarly, end 234 of ear frame member 230 is coupled to end 214 of the band 210 at connection 242. While the band and the ear frame members are made of a resilient material, such as plastic, any suitable material may be used. Connections 240 and 242 may be formed using any conventional method, such as welding, stamping or heating.

Figure 11:
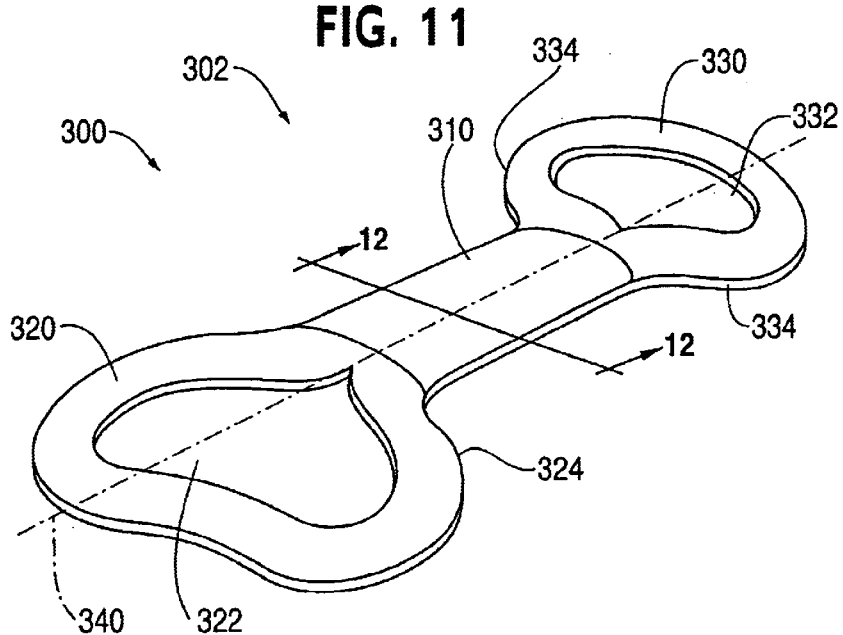
FIG. 11 illustrates perspective view of a frame, in an extended configuration, for use in constructing an ear warmer, according to an embodiment of the present invention.
Figure 13:
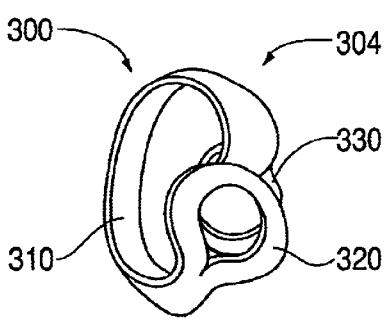
FIG. 13 illustrates the frame of FIG. 11 in a collapsed configuration, according to another embodiment of the present invention.
Figure 12:
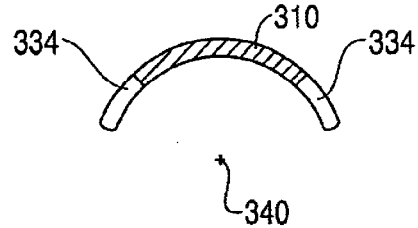
FIG. 12 illustrates a cross-sectional view of the frame of FIG. 11 taken along the lines "12—12" in FIG. 11.

FIGS. 11–13 illustrate a frame for use in constructing an ear warmer, according to another embodiment of the present invention. Frame 300 is selectively disposable in multiple configurations. Frame 300 has a curved shape, as discussed in more detail below, that facilitates the disposing of the frame 300 in particular configurations.

Frame 300 may be disposed in an expanded or extended configuration as illustrated in FIG. 11. As illustrated, frame 300 maintains an extended or linear shape along its longitudinal axis while in its extended configuration. Frame 300 may also be disposed in a collapsed configuration as illustrated in FIG. 13. Frame 300 may be easily stored and/or transported while in the collapsed configuration. Frame 300 may be disposed in multiple intermediate configurations (not illustrated) when the user is wearing the ear warmer.

In the illustrated embodiment, frame 300 includes a middle portion 310 and ear portions 320 and 330 coupled to the middle portion 310. In this embodiment, ear portions 320 and 330 are integrally formed with the middle portion 310.

Ear portion 320 includes a loop portion and defines an opening or ear-hole aperture 322. The ear portion 320 includes an outer surface 324 that defines the perimeter of the ear portion 320. Ear portion 330 includes a loop portion and defines an opening or ear-hole aperture 332. The ear portion 330 includes an outer surface 334 that defines the perimeter of the ear portion 330.

In the illustrated embodiment, frame 300 has a curved shape. The frame 300 is curved about an axis 340 extending along the length of the frame 300 as illustrated in FIG. 12. Frame 300 is curved about axis 340 for a sufficient distance to enable the frame 300 to snap into either its extended configuration or its collapsed configuration depending on the applied force. When the frame 300 is in its collapsed configuration, the ear portions 320 and 330 can be disposed proximate to each other as illustrated in FIG. 13.

FIG. 14 illustrates a frame for use in constructing an ear warmer, according to another embodiment of the present invention. Frame 400 is conceptually similar to frame 300 in that frame 400 is selectively disposable in multiple configurations. Each component of frame 400 has a curved shape that facilitates the disposing of the frame 400 in particular configurations. Frame 400 may be disposed in extended, intermediate, and collapsed configurations similar to frame 300.

In the illustrated embodiment, frame 400 includes two frame members 410 and 420. In this embodiment, frame members 410 and 420 are structurally similar.

Frame member 410 includes a band or frame portion 412 and an ear portion 416 coupled to the band portion 412. In this embodiment, band portion 412 is integrally formed with the ear portion 416. Band portion 412 includes a connection hole 414 through which a conventional fastener (not shown) is inserted to couple frame members 410 and 420 together. Ear portion 416 defines an opening or ear-hole aperture 418. Frame member 410 is curved about an axis 430 extending along the length of the frame member 410. Axis 430 is substantially parallel to the longitudinal axis of the frame member 410.

Frame member 420 includes a band or frame portion 422 and an ear portion 426 coupled to the band portion 422. In this embodiment, band portion 422 is integrally formed with the ear portion 426. Band portion 422 includes a connection hole 424 through which a conventional fastener (not shown) is inserted to couple frame members 410 and 420 together.

In an alternative embodiment, any of the band portion and the frame members can include an integral or built-in snap connector or rivet. In that arrangement, the other of the band portion and the frame members can include an opening to receive the connector or rivet.

Returning to FIG. 14, ear portion 426 defines an opening or ear-hole aperture 428. Frame member 420 is curved about an axis 432 extending along the length of the frame member 420. Axis 432 is substantially parallel to the longitudinal axis of the frame member 420.

FIG. 15 illustrates a frame for use in constructing an ear warmer, according to another embodiment of the present invention. Frame 500 is conceptually similar to frames 300 and 400 in that frame 500 is selectively disposable in multiple configurations. Each component of frame 500 has a curved shape that facilitates the disposing of the frame 500 in particular configurations. Frame 500 may be disposed in extended, intermediate, and collapsed configurations similar to frames 300 and 400.

In the illustrated embodiment, frame 500 includes a band 510 and ear frame members or portions 520 and 530. Band 510 is coupled to the ear frame members 520 and 530 to form frame 500 for an ear warmer.

Band 510 includes ends 512 and 516 and connection holes 514 and 518 proximate to ends 512 and 516, respectively. Conventional fasteners are inserted through connection holes 514 and 518 to couple the band 510 to the ear frame members 520 and 530. Band 510 is curved about an axis that extends along the length of the band 510.

Ear frame member 520 defines an opening or ear-hole aperture 522 and includes an end 524 with a connection hole 526. Ear frame member 520 can be curved about an axis extending along the length of the ear frame member 520. Similarly, ear frame member 530 defines an opening or ear-hole aperture 532 and includes an end 534 with a connection hole 536. Ear frame member 530 can be curved about an axis extending along the length of the ear frame member 530.

While one, two and three piece ear warmer frames are illustrated in FIGS. 11–15, ear warmer frames may have any number of components connected together. While the components in the embodiments illustrated in FIGS. 11–15 are described as being curved, it is not necessary that all of the components in an ear warmer frame be curved. To create a collapsible ear warmer frame, only the band areas need to be curved. For example, in the frame 500 illustrated in FIG. 15, ear frame members 520 and 530 do not need to be curved if band 510 is curved, as previously described. Various modifications and combinations of curved and straight frame components may be assembled to make an ear warmer frame.

Figure 16:
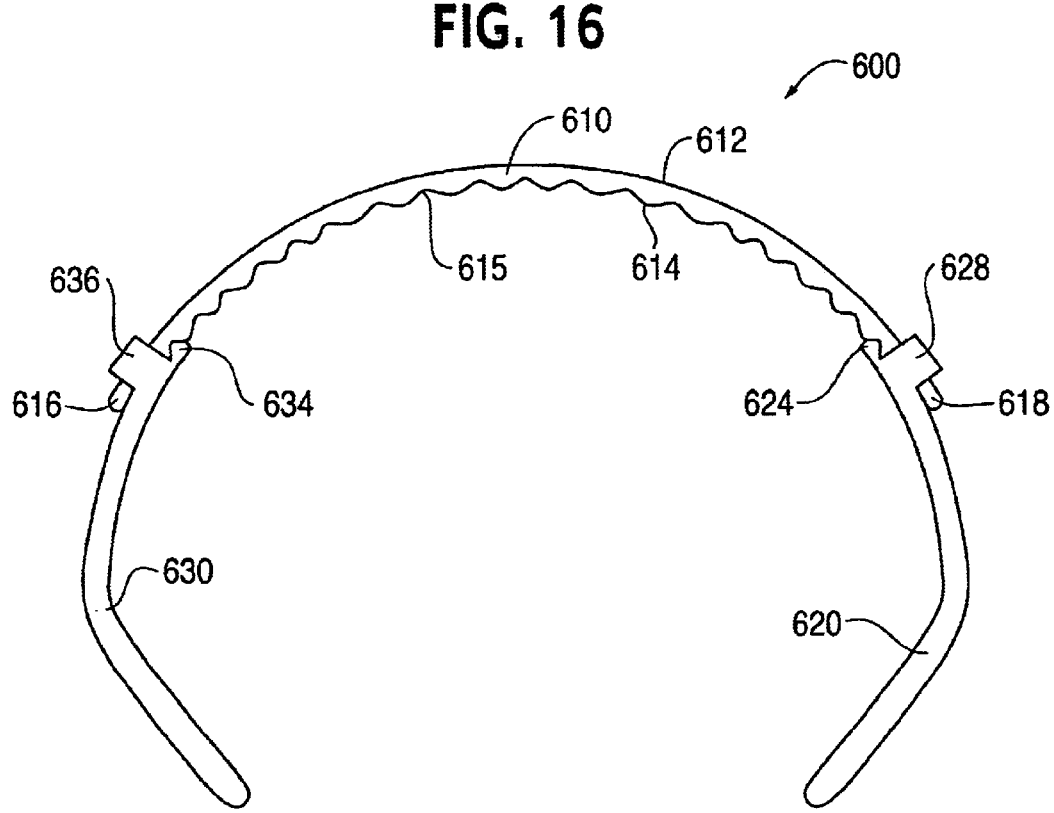
FIG. 16 illustrates an assembled side view of a frame for use in constructing an ear warmer, according to another embodiment of the invention.
Figure 17:
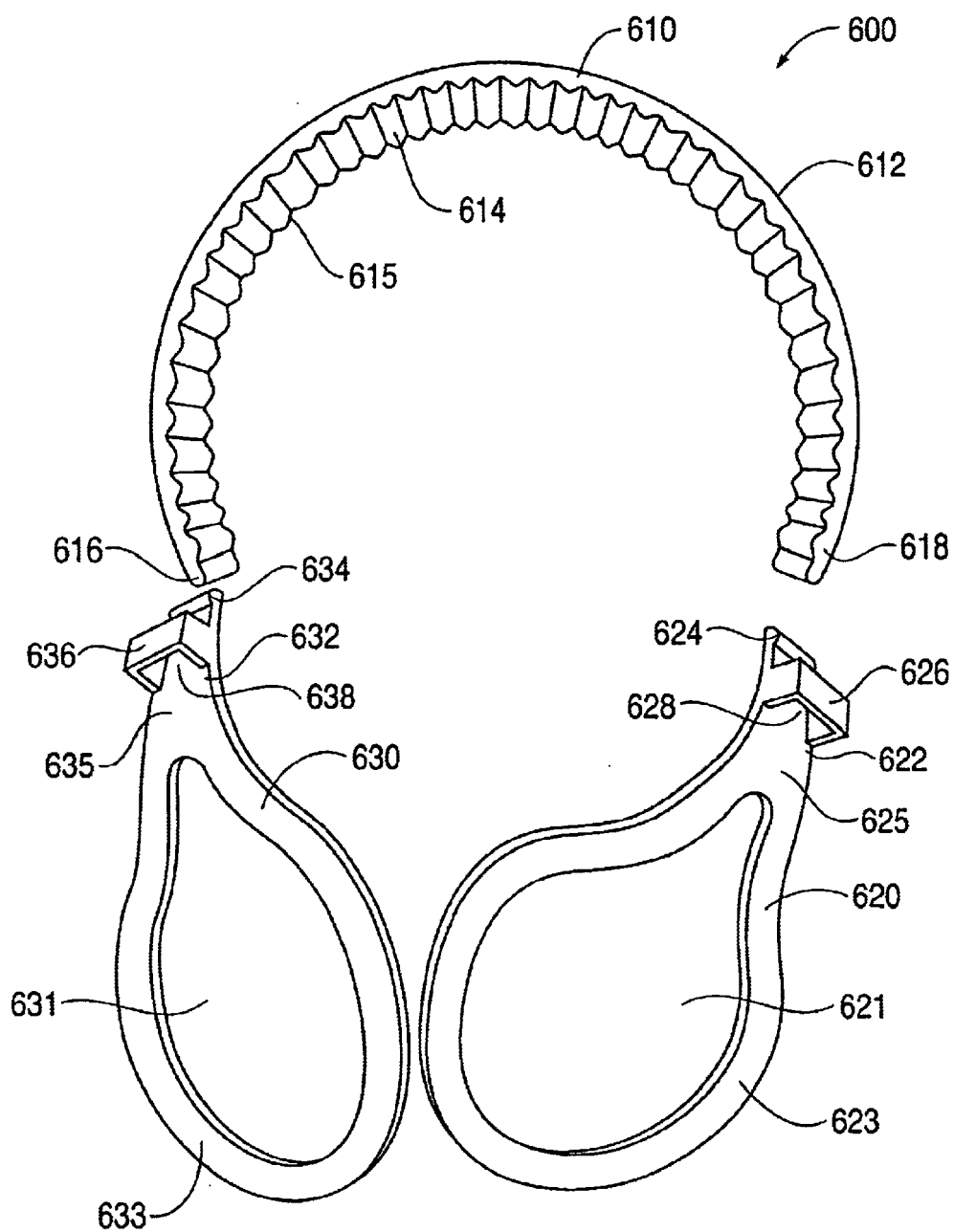
FIG. 17 illustrates an exploded perspective view of the frame of FIG. 16.

FIGS. 16–17 illustrate a frame for use in constructing an ear warmer, according to another embodiment of the present invention. Frame 600 includes several components that move relative to each other to adjust the overall length of the frame 600. In the illustrated embodiment, frame 600 includes a band 610 and ear frame members 620 and 630 that are slidably coupleable to the band 610.

Band 610 with an outer surface 612 and an inner surface 614 and ends 616 and 618. In the illustrated embodiment, band 610 includes ridges or projections 615 formed on the inner surface 614. In an alternative embodiment, the inner surface of the band does not include any ridges or projections. In that embodiment, the band and the ear frame members are retained together by friction.

Returning to FIGS. 16–17, in the illustrated embodiment, ear frame member 620 includes an ear frame portion 623 that defines an opening 621 and a band portion 625 that includes an end 622. A protrusion 624 is disposed proximate to end 622. The ear frame member 620 includes a passageway 626 that forms an opening 628. To couple band 610 to ear frame member 620, end 618 is inserted into opening 628 of passageway 626. Protrusion 624 engages the ridges 614 on the band 610 to retain the ear frame member 620 in a particular position along the band 610.

In the illustrated embodiment, ear frame member 630 includes an ear frame portion 633 that defines an opening 631 and a band portion 635 that includes an end 632. A protrusion 634 is disposed proximate to end 632. The ear frame member 630 includes a passageway 636 that forms an opening 638. To couple band 610 to ear frame member 630, end 616 is inserted into opening 638 of passageway 636. Protrusion 634 engages the ridges 614 on the band 610 to retain the ear frame member 630 in a particular position along the band 610.

In an alternative embodiment, band may include one or more passageways into which ear frame members are inserted. In that embodiment, the ear frame members would not have passageways, respectively. In alternative embodiments, any passageways formed on or coupled to band or ear frame members may be located on the inner surface or outer surface of the band or ear frame members.

Figure 18:
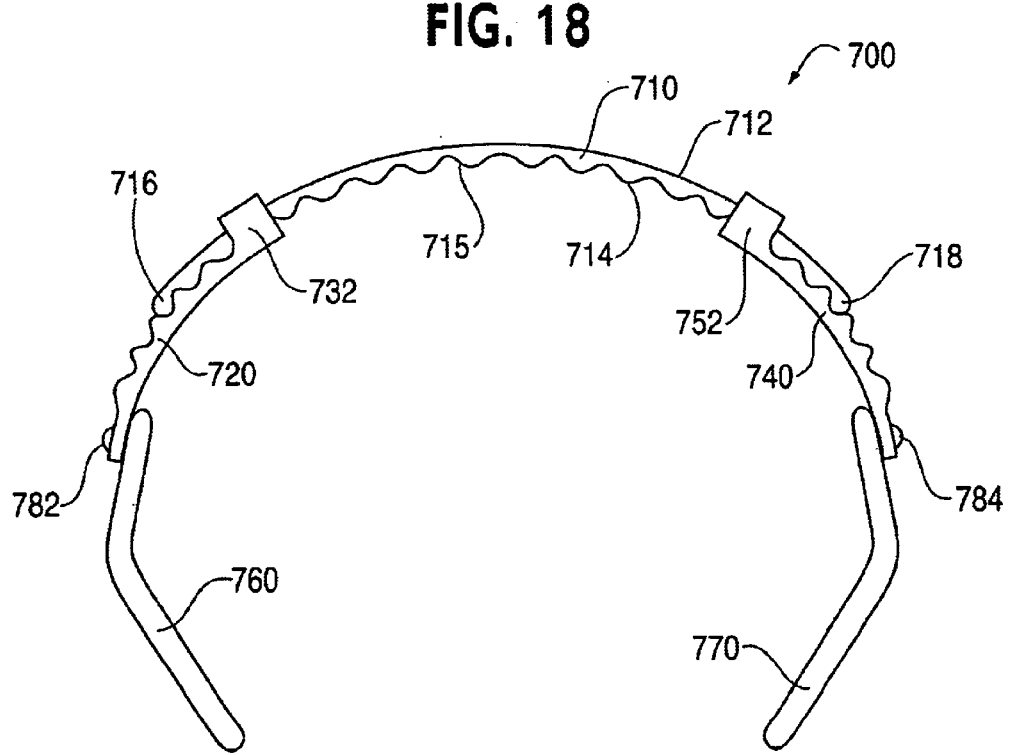
FIG. 18 illustrates an assembled side view of a frame for use in constructing an ear warmer, according to another embodiment of the invention.
Figure 19:
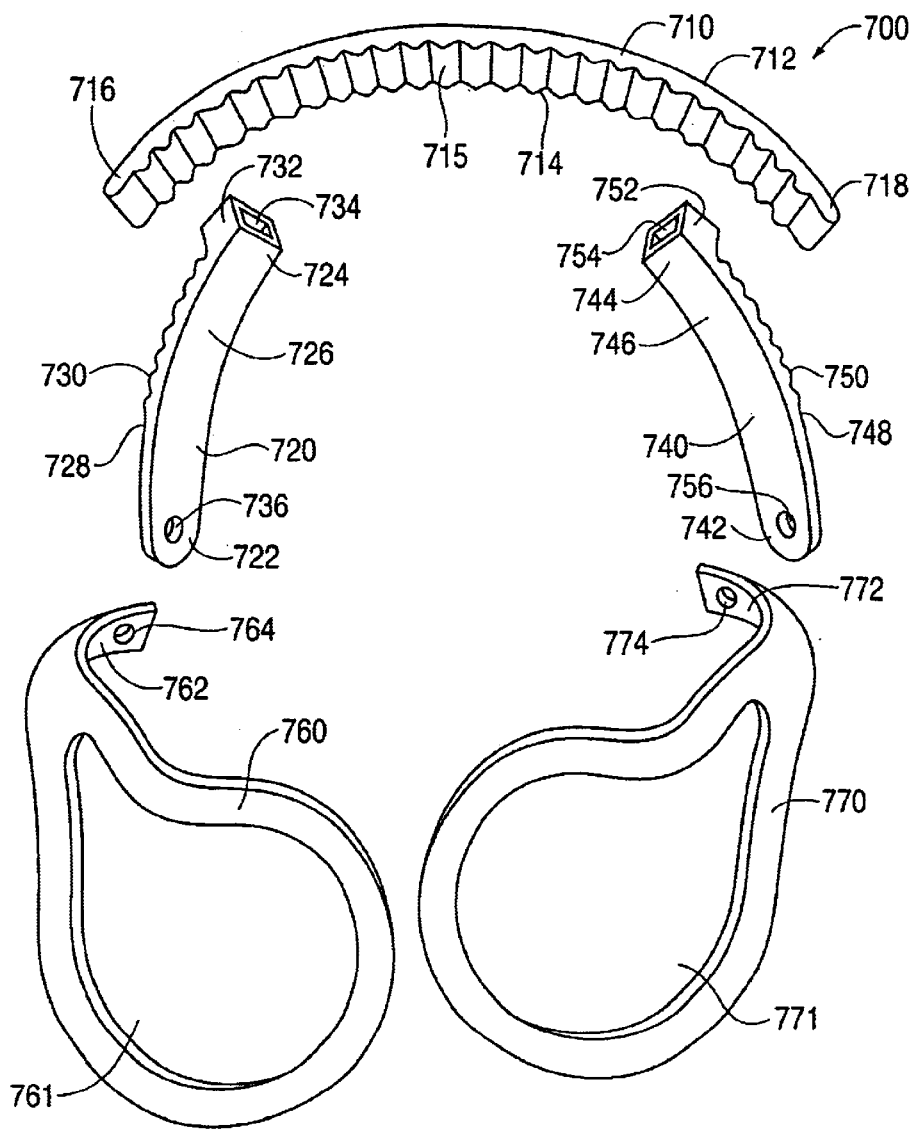
FIG. 19 illustrates an exploded perspective view of the frame of FIG. 18.

FIGS. 18–19 illustrate a frame for use in constructing an ear warmer, according to another embodiment of the present invention. Frame 700 includes several components that move relative to each other to adjust the overall length of the frame 700. In the illustrated embodiment, frame 700 includes a band 710, connector bands 720 and 740, and ear frame members 760 and 770. Connector bands 720 and 740 are slidable coupleable to the band 710.

Band 710 with an outer surface 712, an inner surface 714, and ends 716 and 718. In the illustrated embodiment, band 710 includes ridges 715 formed on the inner surface 714. In alternative embodiments, the inner surface of the band is a smooth surface without any ridges. In that embodiment, the band and the connector bands are retained together by friction.

Returning to FIGS. 18–19, in the illustrated embodiment, connector band or band portion 720 includes an inner surface 726, an outer surface 728, and ends 722 and 724. Connector band 720 includes ridges 730 formed on the outer surface 728. Connector band 720 also includes a passageway 732 that defines an opening 734. A connection opening 736 is located proximate to end 722. A conventional fastener 782 may be inserted into connection opening 736 to couple the connector band 720 and the ear frame member 760. To couple the band 710 to the connection band 720, end 716 is inserted into opening 734 of passageway 732. Ridges 730 on the connection band 720 engage the ridges 715 on the band 710 to retain the connection band 720 in a particular position along the band 710.

In the illustrated embodiment, connector band or band portion 740 includes an inner surface 746, an outer surface 748, and ends 742 and 744. Connector band 740 includes ridges 750 formed on the outer surface 748. Connector band 740 also includes a passageway 752 that defines an opening 754. A connection opening 756 is located proximate to end 742. A conventional fastener 784 may be inserted into connection opening 756 to couple the connector band 740 and the ear frame member 770. To couple the band 710 to the connection band 740, end 718 is inserted into opening 754 of passageway 752. Ridges 750 on the connection band 740 engage the ridges 715 on the band 710 to retain the connection band 740 in a particular position along the band 710.

In an alternative embodiment, band may include one or more passageways into which connector bands are inserted. In that embodiment, the connector bands would not have passageways, respectively. In alternative embodiments, any passageways formed on or coupled to band or connector bands may be located on the inner surface or outer surface of the band or connector bands.

Ear frame member 760 defines an opening 761 and includes an end 762. The ear frame member 760 includes a connection opening 764 located proximate to end 762. A conventional fastener 782 can be inserted into connection openings 736 and 764 to couple the connection band 720 and the ear frame portion 760 together.

Ear frame member 770 defines an opening 771 and includes an end 772. The ear frame member 770 includes a connection opening 774 located proximate to end 772. A conventional fastener 784 can be inserted into connection openings 756 and 774 to couple the connection band 740 and the ear frame portion 770 together.

While frame members 760 and 770 are coupled to the connection bands 720 and 740 using fasteners, any conventional coupling method or technique can be used.

Figure 20:
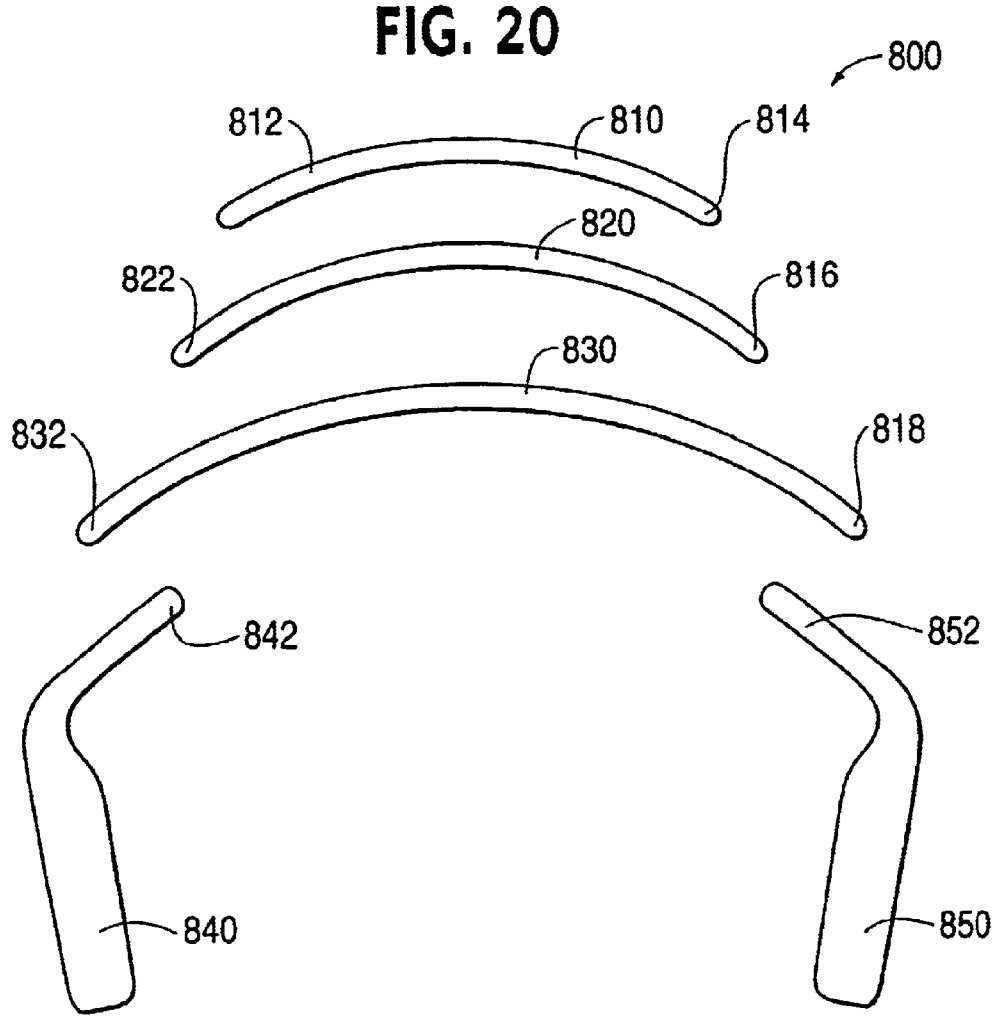
FIG. 20 illustrates a frame set for use in constructing an ear warmer, according to another embodiment of the invention.

FIG. 20 includes a frame set or combination for use in constructing an ear warmer, according to another embodiment of the present invention. Frame set 800 includes several bands 810, 820 and 830 and ear frames or ear frame members 840 and 850. Each band 810, 820, and 830 is coupleable to ear frame members 840 and 850.

In the illustrated embodiment, bands 810, 820 and 830 have different lengths and are interchangeable to construct an ear warmer frame for insertion into an ear warmer shell to form an ear warmer. The different lengths of bands 810, 820 and 830 enable a user to change the overall length of the ear warmer. Similarly, multiple users with different sized heads can use the same ear warmer by interchanging the different length bands 810–830.

In one arrangement, band 810 includes ends 812 and 814 that can be coupled to ends 842 and 852 of ear frame members 840 and 850, respectively. In an alternative arrangement, band 820 inlcudes ends 822 and 816 that can be coupled to the ear frame member ends 842 and 852, respectively. In another arrangement, band 830 inlcudes ends 832 and 818 that can be coupled to the ear frame member ends 842 and 852, respectively. The ends may be coupled to using any conventional fastener or other method. For example, the ends may be coupled using a release-type mechanism that facilitates the disconnection of a band and reconnection of another band to the ear frame members.

Figure 21:
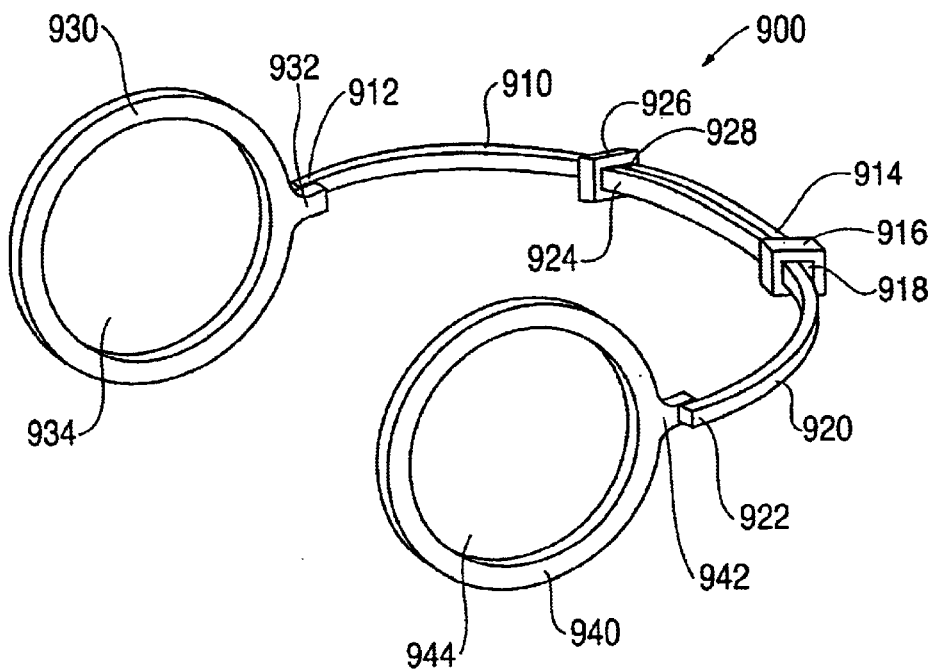
FIG. 21 illustrates a perspective view of a frame for use in constructing an ear warmer, according to another embodiment of the invention.
Figure 22:
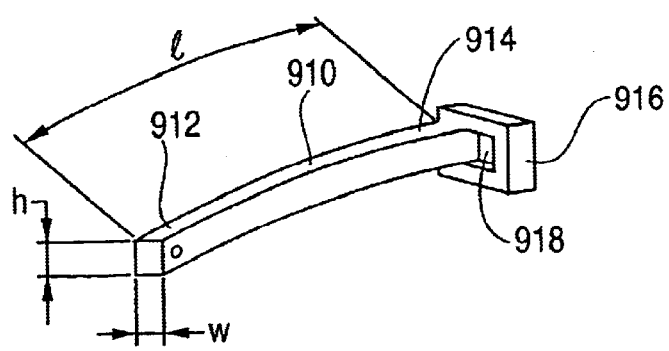
FIG. 22 illustrates a perspective view of a frame member of the frame of FIG. 21.

FIGS. 21–22 illustrate a frame for use in constructing an ear warmer, according to another embodiment of the present invention. Frame 900 includes several bands 910 and 920 and ear frame members 930 and 940. Ear frame member 930 is coupled to band 910 and ear frame member 940 is coupled to band 920. Bands 910 and 920 are slidably coupled to each other.

In the illustrated embodiment, band 910 includes ends 912 and 914 and a passageway 916 located proximate to end 914 (see FIG. 22). Passageway 916 includes an opening 918 through which band 920 is inserted. Band 920 includes ends 922 and 924 and a passageway 926 located proximate to end 924. Passageway 926 includes an opening 928 through which band 910 is inserted.

Ear frame member 930 includes an end 932 and defines an opening 934. End 932 is coupled to end 912 of the band 910 using any conventional technique, such as a fastener (not shown). Similarly, ear frame member 940 includes an end 942 and defines an opening 944. End 942 is coupled to end 922 of the band 920 using any conventional technique, such as a fastener.

A variety of methods may be used to assemble the frame 900. For example, end 912 of band 910 is inserted into opening 928 of the passageway 926 at the same time that end 922 of band 920 is inserted into opening 918 of the passageway 916. Ear frame members 930 and 940 are connected to ends 912 and 922 of bands 910 and 920, respectively. The openings 918 and 928 are sized so that the bands 910 and 920 are frictionally retained therein after moved by the user.

As illustrated in FIG. 22, each of the bands 910 and 920 has a substantially square cross-section. In the illustrated embodiment, the bands 910 and 920 have the same structure. The width (w), the height (h), and the length (l) dimensions of the band 910 are illustrated in FIG. 22. The size and shape of the band 910 may vary. In this embodiment, the width (w) of each band is approximately the same as the height (h) of each band. In alternative embodiments, the width (w) of each band may be greater than the height (h) of each band. Also, in another embodiment, band 910 may have different dimensions than band 920.

Many conventional bands for ear warmers have rectangular cross-sections. The bands 910 and 920 are shorter in height and narrower in width than conventional bands, thereby reducing the amount of material and the overall weight of the ear warmer frame 900. Frame 900 is a light-weight and low-cost frame that can be used to construct an ear warmer.

The size and shape of the frame and the particular frame material used are relevant factors relating to characteristics of an ear warmer frame, such as strength, elasticity, and durability. The strength of an ear warmer frame affects the ability of the frame to maintain a configuration that supports the ear warmer on a wearer's head. If the size of an ear warmer frame is reduced such that the frame cannot stay on the wearer, then other characteristics of the frame can be changed. For example, the shape of the frame may be changed to a configuration with increased strength. Alternatively, the material may be changed to a material with increased stiffness and rigidity.

Figure 23:
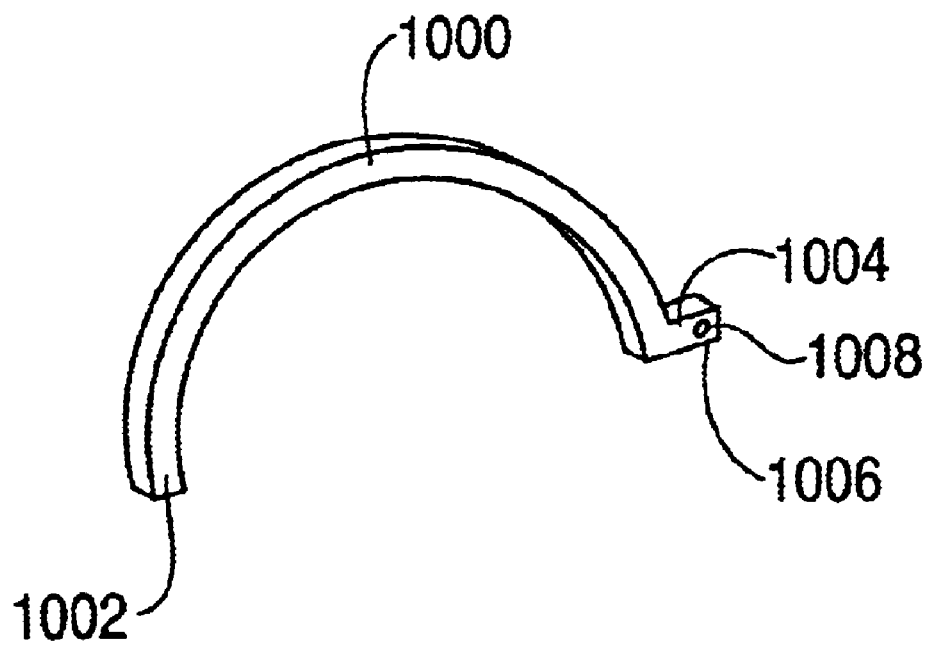
FIG. 23 illustrates a perspective view of an ear frame member of a frame for use in constructing an ear warmer, according to another embodiment of the invention.

FIG. 23 illustrates an ear warmer member for use in constructing an ear warmer, according to another embodiment of the present invention. In the illustrated embodiment, the ear frame member 1000 has an arcuate configuration, as opposed to a complete circular or oval configuration. The ear frame member 1000 includes ends 1002 and 1004. End 1004 includes an extension 1006 that defines a connection opening 1008 that can be used to couple the ear warmer member 1000 to a band or other portion of a frame.

In one embodiment, one or two ear frame members 1000 can be used with the frame 900 illustrated in FIGS. 21 and 22. Because ear frame members 1000 have less material than ear frame members 930 and 940, the weight of a frame 900 is further reduced.

While the components of the ear warmer frames disclosed herein are made from plastic, any suitable material that has sufficient stiffness or rigidity to support the ear warmer on a wearer's head may be used.

In alternative embodiments, the components of the ear warmer frames, including the frames, frame members, frame portions, bands, connector bands, band portions, and band members, can have any cross-sectional shape. For example, the cross-section of any of the ear warmer frame components may resemble a square, rectangle, circle, oval, an arc, or other geometric shape.

While the invention has been described in detail and with reference to specific embodiments thereof, it will be apparent to one skilled in the art that various changes and modifications may be made therein without departing from the spirit and scope thereof. Thus, it is intended that the present invention covers the modifications and variations of this invention provided they come within the scope of the appended claims and their equivalents.

What is claimed is:

1. An ear warmer, comprising:

a shell; and a frame configured to be inserted into said shell, said frame including a first ear portion and a second ear portion, said frame being selectively disposable in an extended configuration and in a collapsed configuration, said first ear portion being proximate to said second ear portion in said collapsed configuration, said frame having a longitudinal axis, said frame being curved about an axis substantially parallel to said longitudinal axis in the extended configuration.

2. The ear warmer of claim 1, wherein said frame includes a first band member and a second band member, said first band member being coupled to said second band member, said first band member including a first frame portion and said first ear portion, and said second band member including a second frame portion and said second ear portion.

3. The ear warmer of claim 1, wherein said frame includes a first band member and a second band member, said first band member being coupled to said second band member, said first band member including a first frame portion and said first ear portion, said second band member including a second frame portion and said second ear portion, said first frame portion being configured to be coupled to said second frame portion.

4. The ear warmer of claim 1, wherein said frame includes a first band member, a second band member, and a third band member, said first band member configured to be coupled to said second band member, and said second band member configured to be coupled to said third band member.

5. The ear warmer of claim 1, wherein said frame includes a first band member, a second band member, and a third band member, said first band member configured to be coupled to said second band member, said second band member configured to be coupled to said third band member, said first band member includes said first ear portion, said second band member includes said second ear portion, and said third band member includes a first frame portion.

6. The ear warmer of claim 5, wherein said first band member has its own longitudinal axis, said second band member has its own longitudinal axis, said first band member being curved about an axis substantially parallel to said longitudinal axis for said first band member, and said second band member being curved about an axis substantially parallel to said longitudinal axis for said second band member.

7. The ear warmer of claim 1, wherein said first ear portion includes a first frame portion defining a first ear-hole aperture, and said second ear portion includes a second frame portion defining a second ear-hole aperture.

8. The ear warmer of claim 1, wherein said frame has a longitudinal axis, said frame being curved about an axis substantially perpendicular to said longitudinal axis when said frame is in said collapsed configuration, and said frame extending along said longitudinal axis when said frame is in said extended configuration.

9. The ear warmer of claim 1, wherein said frame maintains an extended shape along said longitudinal axis while in said extended configuration.

10. An ear warmer, comprising:

a shell including:

an outer membrane defining a perimeter, said outer membrane having a first side and a second side, said second side being opposite to said first side of said outer membrane; and an inner membrane defining a perimeter, said inner membrane having a first side and a second side, said second side of said inner membrane being opposite to said first side of said inner membrane, said inner membrane first side being attached to said outer membrane first side along a first fixedly coupled portion, said inner membrane second side being attached to said outer membrane second side along a second fixedly coupled portion, at least a portion of said first fixedly coupled portion and at least a portion of said second fixedly coupled portion being disposed within an interior of the ear warmer; and a frame configured to be inserted into said shell.

11. The ear warmer of claim 10, wherein said first fixedly coupled portion includes a weld.

12. The ear warmer of claim 10, wherein said frame includes a band member, a first ear frame member, and a second ear frame member, said first ear frame member being fixedly coupled to said band member, and said second ear frame member being fixedly coupled to said band member.

13. The ear warmer of claim 12, wherein said first ear frame member is welded to said band member.

14. An ear warmer, comprising:

a shell having an interior; and a frame disposed within the interior of said shell, said frame being unitarily formed and including a first ear portion, a second ear portion and a middle portion, said first ear portion of the frame being substantially circular in shape and defining an opening, said second ear portion of the frame being substantially circular in shape and defining an opening, said middle portion of the frame being disposed between said first ear portion of the frame and said second ear portion of the frame.

15. The ear warmer of claim 14, wherein said shell inlcudes an inner membrane and an outer membrane coupled to the inner membrane.

16. The ear warmer of claim 14, wherein said frame is selectively disposable in an extended configuration and in a collapsed configuration, said first ear portion of the frame being proximate to said second ear portion of the frame when said frame is in its collapsed configuration.

17. The ear warmer of claim 14, wherein the openings defined by said first ear portion and said second ear portion are substantially circular in shape.

18. The ear warmer of claim 14, wherein said shell having a first membrane and a second membrane, the first membrane including a perimeter, a first substantially circular ear portion, a second substantially circular ear portion and a middle portion disposed between the first and the second substantially circular ear portions of the first membrane, the second membrane including a perimeter, a first substantially circular ear portion, a second substantially circular ear portion and a middle portion disposed between the first and the second substantially circular ear portions of the second membrane, at least a portion of the perimeter of the first membrane being coupled to at least a portion of the perimeter of the second membrane.

19. An ear warmer, comprising:

a shell having an interior; and a frame disposed within the interior of said shell, said frame being unitarily formed and including a first ear portion, a second ear portion and a middle portion, the first ear portion of the frame having a loop portion, the loop portion of the first ear portion including a first end and a second end disposed proximate to the first end of the loop portion of the first ear portion, said second ear portion of the frame having a loop portion, the loop portion of the second ear portion including a first end and a second end disposed proximate to the first end of the loop portion of the second ear portion, the middle portion of the frame being disposed between the first ear portion of the frame and the second ear portion of the frame.

20. The ear warmer of claim 19, wherein said shell has a first membrane and a second membrane, the first membrane including a perimeter, a first substantially circular ear portion, a second substantially circular ear portion and a middle portion disposed between the first and the second substantially circular ear portions of the first membrane, the second membrane including a perimeter, a first substantially circular ear portion, a second substantially circular ear portion and a middle portion disposed between the first and the second substantially circular ear portions of the second membrane, at least a portion of the perimeter of the first membrane being coupled to at least a portion of the perimeter of the second membrane.

21. The ear warmer of claim 19, wherein the loop portion of the first ear portion is substantially circular in shape.

* * * * *